US00PP23059P3

(12) United States Plant Patent
Korlipara

(10) Patent No.: US PP23,059 P3
(45) Date of Patent: Sep. 18, 2012

(54) *ECHINACEA* PLANT NAMED 'NOW CHEESIER'

(50) Latin Name: ***Echinacea* spp.**
Varietal Denomination: Now Cheesier

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 99 days.

(21) Appl. No.: 12/931,236

(22) Filed: Jan. 26, 2011

(65) Prior Publication Data
US 2012/0192326 P1 Jul. 26, 2012

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Now Cheesier' characterized by large yellow orange inflorescences, a medium habit with good branching, strong stems, and excellent vigor.

1 Drawing Sheet

Botanical denomination: *Echinacea* spp.
Variety designation: 'Now Cheesier'.

The present invention relates to a new and distinct cultivar of *Echinacea* and given the cultivar name 'Now Cheesier'. *Echinacea* is in the family Asteraceae. This new cultivar is a third generation seeding originating from a planned breeding program using *Echinacea paradoxa* (an unpatented plant) as the seed parent in the original cross and *Echinacea purpurea* 'Ruby Giant' (an unpatented plant) as the pollen parent. The exact parents of this selection are unknown, unnamed, proprietary plants.

Compared to *Echinacea* 'Mac 'n' Cheese' (U.S. Plant Pat. No. 19,464), the most similar plant on the market, the new variety is more vigorous, has more crowns, and has larger inflorescences.

Compared to *Echinacea* Harvest Moon™ ('Matthew Saul' U.S. Plant Pat. No. 17,652), the new variety has longer and wider ray florets.

This new *Echinacea* cultivar is distinguished by:

1. large yellow orange inflorescences,
2. a medium habit with good branching,
3. strong stems, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the inflorescences of *Echinacea* 'Now Cheesier' on a one-year-old plant growing in the field in full sun in early July in Canby, Oreg.

DETAILED PLANT DESCRIPTION

The following is a detailed description of the new *Echinacea* cultivar based on observations of 18-month-old specimens growing in the garden in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:
- *Type.*—Herbaceous perennial.
- *Hardiness.*—USDA Zones 4 to 9.
- *Size.*—Grows to about 43 cm wide and 64 cm tall to top of inflorescences.
- *Form.*—Basal clump, with about 6 stems from the base.
- *Vigor.*—Excellent.
- *Roots.*—Fibrous, with many downward growing and few laterals, ivory in color, Yellow White 158D, roots develop easily from cuttings from the crown.

Stem (flowering):
- *Type.*—Ascending, with 1 to 6 inflorescences per stem.
- *Size.*—To 62 cm tall to a terminal inflorescence and 10 mm wide at base.
- *Internode length.*—1 cm to 9 cm.
- *Surface texture.*—Strigose.
- *Color.*—Yellow Green 146B.

Leaf (basal):
- *Type.*—Simple.
- *Shape.*—Lanceolate.
- *Arrangement.*—Basal.
- *Blade size.*—Grows to 15 cm long and 4.5 cm wide.
- *Margins.*—Sparsely serrate, slightly undulate.
- *Apex.*—Acute.
- *Base.*—Attenuate.
- *Surface texture.*—Strigose on both sides.
- *Venation.*—Pinnate, with 3 main veins.
- *Color.*—Topside Yellow Green 147A bottom side Yellow Green 147B.

*Petiole description.*—Grows to 13 cm long and 2.5 mm wide, strigose, Yellow Green 147C.

Leaf (stem):

*Type.*—Simple.

*Shape.*—Lanceolate.

*Arrangement.*—Alternate.

*Blade size.*—Grows to 12 cm long and 4 cm wide.

*Margins.*—Entire to sparsely serrate, somewhat undulate.

*Apex.*—Acute.

*Base.*—Attenuate.

*Surface texture.*—Strigose on both sides.

*Venation.*—Pinnate, with 3 main veins from the base.

*Color.*—Topside Yellow Green 147A, bottom side Yellow Green 147B.

*Petiole description.*—On lowermost leaves only, clasping, grows to 8 cm long and 5 mm wide above the clasp, glabrous, Yellow Green 147C.

Inflorescence:

*Type.*—Composite on terminal stalked heads.

*Number of flowering stems per plant.*—About 6.

*Flowering stem.*—Grows to 62 cm tall from the base of the plant to the terminal inflorescence and can grow to 19 cm long from the top stem leaf to the base of an inflorescence; branched with 1 to 6 inflorescences per stem; diameter growing to 9 mm wide near the inflorescence; strigose; Yellow Green 144A.

*Size.*—Grows to 14 cm wide and 5.5 cm deep as disc enlarges.

*Form.*—Ray florets held slightly reflexed, mature disc is conic.

*Immature inflorescence.*—Grows to 3 cm wide and 2.5 cm deep, ray florets held upright and rolled up so only the back color shows, Yellow 11B, disc color Yellow Green 146A.

*Ray florets.*—Without pistil or stamen, about 20 full size in number (and 4 to 9 smaller rays growing at irregular angles), grow to 60 mm long and 14 mm wide, oblanceolate with the tip two to three-toothed (each acute), entire margins, base attenuate, glabrous on both sides; topside Yellow Orange 23A maturing to Yellow Orange 15A, bottom side Yellow Orange 15B with edges Yellow Orange 23A.

*Disc.*—Flat becoming conic, becoming 36 mm deep and 45 mm wide with maturity, Yellow Green 146A in the background and Yellow Orange 23A in the foreground.

*Disc florets.*—About 330 in number, each with 1 pistil and 4 stamen, grow to 10 mm long and 2 mm wide, each with one persistent, very stiff linear bract (14 mm long with the top 4 mm colored Yellow Orange 23A on tip then Yellow Green 144A in middle, then Yellow Green 145D on bottom ⅓); corollas 6 mm long and 1.5 mm wide, tubular, 5 lobed, glabrous, Yellow Green 145D except lobes where Yellow Green 144A; pistil 10 mm long, ovary 2.8 mm long, White NN155D, style 5 mm long Yellow Green 145D, 2-branched stigma spreading, Yellow Green 151B; stamen 7 mm long, filaments 4 mm long and Yellow Green 145D, anthers 3 mm long and Greyed Purple N186A, pollen Yellow Orange 23A.

*Phyllaries.*—In 4 leafy series, area grows to 40 mm wide and 15 mm deep, lobes lanceolate in shape, reflexed, grow to 16 mm long and 4 mm wide, Yellow Green 147B, margins strigose, tip acute, strigose on both sides.

*Receptacle.*—Grows to 15 mm wide and 16 mm deep, White 155B.

*Bloom period.*—July through October in Canby, Oreg.

*Fragrance.*—Excellent, floral.

*Lastingness.*—Each inflorescence lasts about two weeks in Canby, Oreg.

Seeds: 3 mm long and 2.5 mm wide, oval, Brown 200C.

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

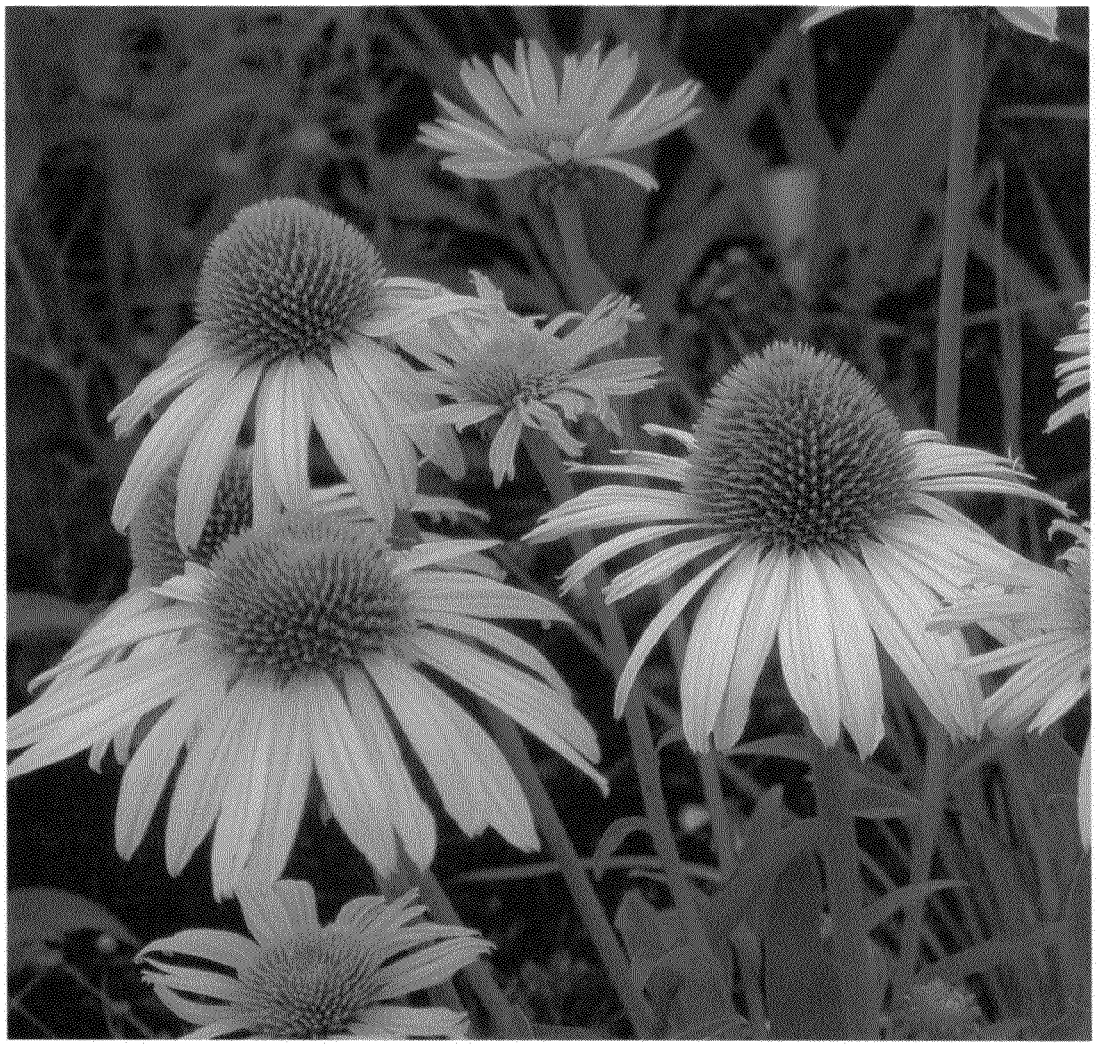

* * * * *